United States Patent [19]
Makovich

[11] Patent Number: 4,523,910
[45] Date of Patent: Jun. 18, 1985

[54] METHOD AND APPARATUS FOR INJECTING MEDICATION INTO A BODY THROUGH A TOOTH

[76] Inventor: Joseph J. Makovich, 67 Old Ridgefield Rd., Wilton, Conn. 06897

[21] Appl. No.: 462,677

[22] Filed: Jan. 31, 1983

[51] Int. Cl.³ .............................................. A61C 17/02
[52] U.S. Cl. ........................................ 433/80; 433/81; 433/215; 433/224; 604/212
[58] Field of Search .................. 433/80, 81, 215, 224, 433/175, 178, 229; 604/181, 182, 212, 213, 214, 215, 216

[56] References Cited

U.S. PATENT DOCUMENTS

| | | | |
|---|---|---|---|
| 881,469 | 3/1908 | Hale | 433/81 |
| 2,258,883 | 10/1941 | Cressler | 433/80 |
| 2,436,623 | 2/1948 | Zile | 433/81 |
| 2,611,956 | 9/1952 | Coleman | 433/178 |
| 2,674,247 | 4/1954 | McLellan | 604/213 |
| 3,079,690 | 3/1963 | Lodige | 433/81 |
| 3,084,435 | 4/1963 | Hass et al. | 433/229 |
| 3,343,263 | 9/1967 | Henlotter | 433/175 |
| 3,704,520 | 12/1972 | Weissman | 433/224 |
| 3,736,933 | 6/1973 | Szabo | 604/212 |
| 4,021,921 | 5/1977 | Detaille | 433/80 |
| 4,400,160 | 8/1983 | Lustig et al. | 433/224 |
| 4,412,825 | 11/1983 | Tokarz | 433/229 |

FOREIGN PATENT DOCUMENTS

| | | | |
|---|---|---|---|
| 294164 | 1/1954 | Switzerland | 433/81 |
| 220491 | 8/1924 | United Kingdom | 433/224 |

Primary Examiner—John J. Wilson
Attorney, Agent, or Firm—Edward R. Hyde

[57] ABSTRACT

A method and apparatus for introducing medicinal fluids into a living body without puncturing the skin. This is done through a root canal of a tooth. A valve device is inserted in the tooth crown and connects to a reservoir of medicinal fluid in the mouth. Pressure on the reservoir will cause fluid to pass from the reservoir through the valve device and root canal into the body tissue.

7 Claims, 4 Drawing Figures

U.S. Patent   Jun. 18, 1985   4,523,910
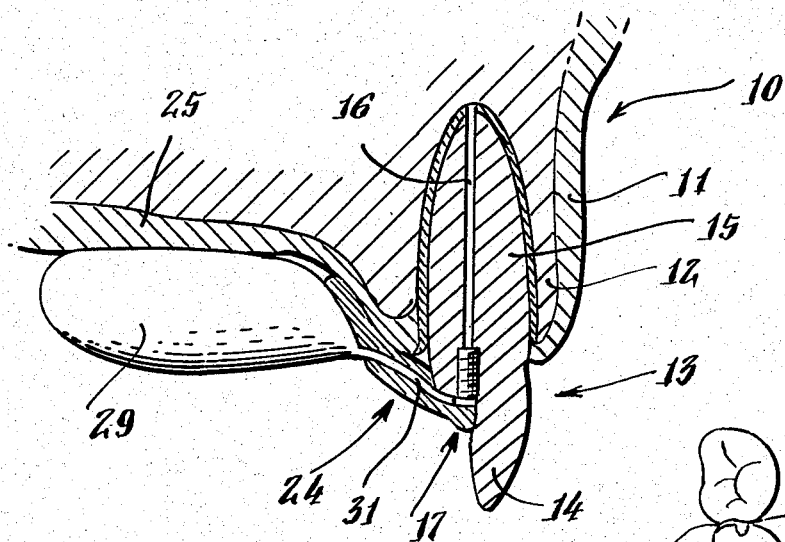
Fig. 1.
Fig. 2.
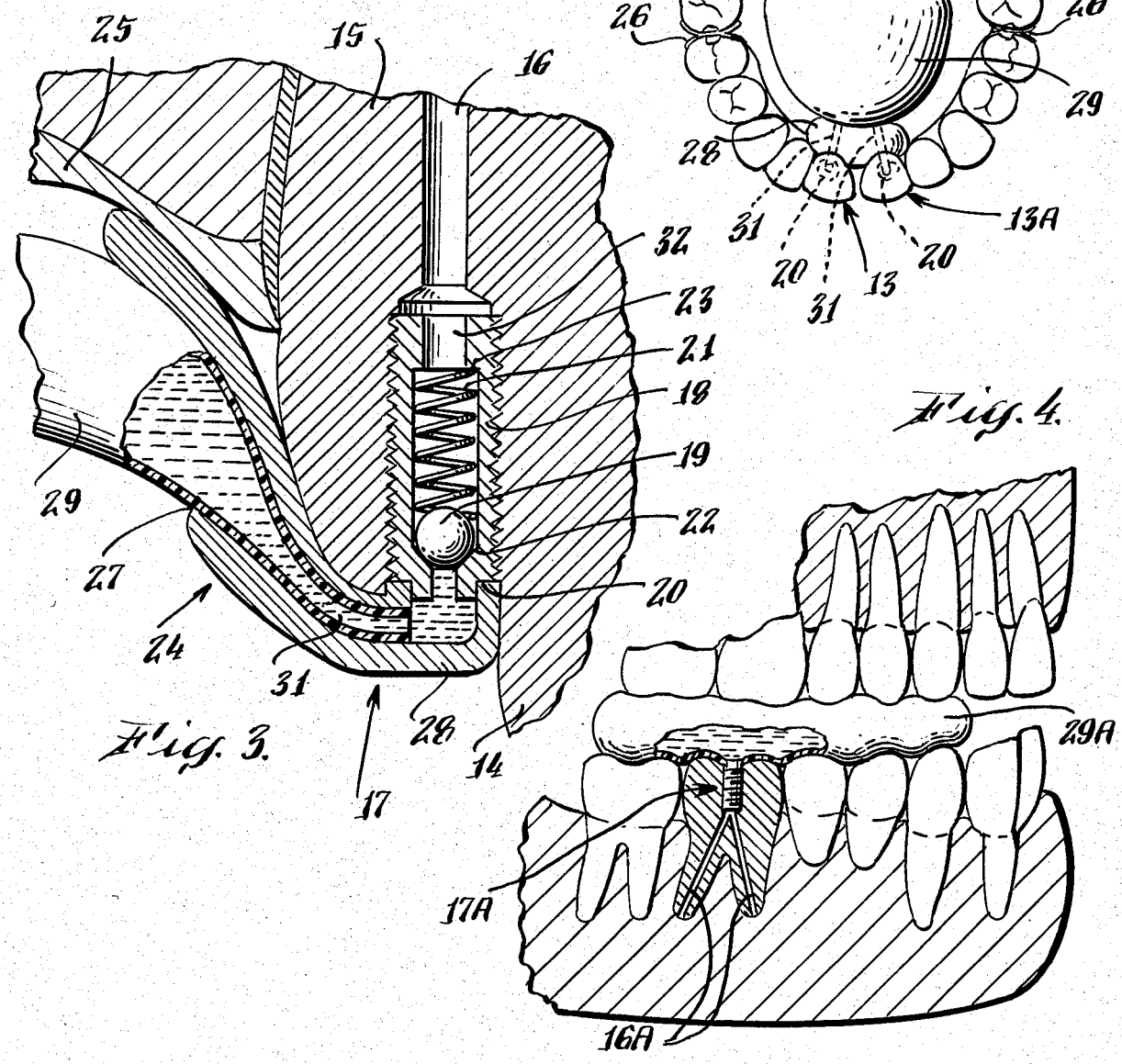
Fig. 3.
Fig. 4.

METHOD AND APPARATUS FOR INJECTING MEDICATION INTO A BODY THROUGH A TOOTH

BACKGROUND OF THE INVENTION

The present invention relates to apparatus and to a method for introducing prescribed medicinal or other fluid from outside the body into the body.

A conventional method for doing this has been by hypodermic needle injections, but this has certain disadvantages such as the pain and resulting injuries of the needle puncture to the patient from multiple punctures, especially if medicine is to be administered on numerous occasions over a long period of time.

Various types of medicinal applicators have been proposed for injecting fluid medicine into the body, but these generally rely upon skin puncture.

It is an object of the present invention to provide an apparatus and method for introducing medicine or other fluid into a body without the need to puncture the skin.

Another object of the invention is to provide a method and apparatus for conveniently injecting medicine or other fluid into the body on a regular or periodic basis without puncturing the skin.

A further object of the invention is to provide a method and apparatus including a reservoir of medicine or other fluid for injection into the body without puncturing the skin.

A still further object of the invention is to provide a method and apparatus whereby general body medicine is injected into the body through an open root canal in a tooth thereby eliminating the need to puncture the skin.

A still further object of the invention is to provide a novel method and apparatus including a reservoir of medicinal fluid for controlled injections into the body.

SUMMARY OF THE INVENTION

It is understood that there are a wide variety of ailments requiring periodic dossages of medicine that for various reasons cannot be taken orally. Conventionally these medicines are applied to the body by hypodermic needle injection causing multiple punctures of the skin. These punctures are avoided by the apparatus and method of the present invention.

The invention contemplates the hollowing out of a root canal of a tooth to form an open passageway for the injection of medicine into the body. As used herein the term medicine includes any fluid that it is desired to be injected into the body of a person or animal. After the tooth canal is hollowed out, an appropriate fitting is applied to the tooth in order to inject medicine through the tooth root canal into the body.

THE DRAWINGS

The above and other objects of the invention will become apparent with reference to the following specification and drawings wherein:

FIG. 1 is a cross-section of an upper tooth equipped with an embodiment of the present invention;

FIG. 2 is a view looking upward toward the roof of a mouth equipped with a medicinal reservoir of the present invention;

FIG. 3 is an enlarged cross-section of the apparatus of the present invention; and FIG. 4 is an illustration of another embodiment of the present invention.

DETAILED DESCRIPTION

Referring now to the drawings, numeral 10 indicates the upper portion of a person's mouth showing the gum or gingiva 11, the bone 12, holding a tooth generally indicated by numeral 13 which may be an incisor. The latter consists of a crown 14, and a root 15, having an open root canal, 16. The root canal runs through the approximate center of the tooth from the root end to the crown of the tooth.

It is well known in root canal operations to drill through the crown of the tooth and remove the dental pulp which initially occupies the root canal area. As shown in the drawings the tooth has had a root canal operation in that a channel has been drilled through the tooth crown and the root canal has been thoroughly cleaned of dental pulp leaving a clear and open passageway through the crown and root.

Inserted within the drilled-out passage in the tooth crown as by screw threading is a one-way valve injector 17, more clearly seen in detailed cross section in FIG. 3 The injector has a body portion 18, externally threaded to be conveniently engaged by the inner surface of the drilled out crown passageway in a fluid tight fit. The valve itself has a through passage along its axis which contains a ball seal 19 and spring 21. As shown in FIG. 3, the ball is urged downward against an arcuate shoulder or seat 22, in the lower portion of valve body 18. The remote end of the spring 18 abuts against a square shoulder 23, so that the spring is always in tension, urging the ball valve to a closed position.

In the embodiment shown in FIGS. 1 through 3, there are two teeth, 13 and 13A, that have root canal open passages and each is fitted with an injector 17.

A partial metal denture framework plate 24 is fitted to the roof of the mouth, 25, in a conventional manner as by clips 26. The clips are secured to appropriate teeth to hold the plate in place in the mouth. The clips, 26, may be detached from the teeth and the plate removed from the mouth in the conventional manner of denture plates.

The forward portion of the plate has two medication channels, 27 formed in extentions 28, that friction fit to an annular recess portion 20 of the outer end of valve body 18. Thus the medication channel 27 is aligned with the axial passage in the valve.

The medication reservoir 29, made of a flexible silicone material, for example, is provided having extentions 31 that extend through the extentions 28, of the partial plate. The flexible reservoir may be removably cemented to the outer surface of the plate 24.

Thus it is seen that the denture framework plate 24 clipped to the teeth carries a flexible medicinal reservoir having two channels 31, through which the medicine may pass out of the reservoir. These channels are held in place by the extentions 28 of the metal plate which extentions connect to the valve injector 17. In its normal condition, the valve mechanism is closed with the spring 21 holding the ball 19 against the curved ball seat 22.

When the person desires to take the medication into his body, he need only apply upward pressure to the flexible reservoir with his tongue. This pressure on the reservoir will be transmitted by fluid's action of the medicine to the ball valve mechanism.

The ball will open and a quantity of fluid will pass through the passage 32 of the valve device, through the cleared out root canal 16 into the body. When tongue pressure is released from the flexible reservoir, the ball valve will close by the action of the spring 21.

Although the embodiment described above contemplates two teeth with root canals for the intake of medicinal fluid, this is only by way of example. It might be only one tooth or alternatively more than two that serve as root canal intakes for the fluid.

The reservoir may be conveniently filled by the person removing the plate 24 from the mouth at which time the extention ends 28 separate from the injector. The reservoir is then removed from the plate and filled in any convenient manner with a further supply of medicinal fluid.

Although the invention has been described with respect to a particular one way ball valve, this is simply by way of example. Any convenient type of one-way valve may be used. Particularly appropriate would be a fixed measured volume valve of conventional type that would inject a predetermined volume of fluid into the tooth upon application of pressure to the reservoir.

Another embodiment of the invention is shown in FIG. 4, in which an injector 17A of the type above described is inserted in a tooth that has two root canals 16A. A flexible reservoir 29A similar in construction to 29 is located between the upper and lower teeth and connected to the intake end of the valva 17A. In this embodiment the flexible silicon reservoir fits directly to the end of the valve device 17A in a friction, fluid-tight jet.

From the above, it is seen that this invention contemplates the injection of a general medicinal fluid into the body through a cleaned out root canal, as an alternative to oral or needle intake of fluid to the body.

Although the invention has been described with respect to a specific embodiment thereof, it is understood that various modifications may be made within the scope of the invention as set forth in the appended claims.

What is claimed is:

1. Apparatus for introducing medicinal fluid into the blood stream of a living body that has a tooth with an unobstructed root canal passing from the tooth crown to the end of the root comprising:
   fluid input means adapted to be secured to the crown portion of a tooth in communication with an unobstructed root canal passing to the end of the root in communication with the living body tissue;
   said fluid input means including a flexible reservoir means adapted to contain medicinal fluid;
   said fluid input means being further adapted to be located entirely within the body mouth in back of the tooth line; and
   said fluid input means being selectively operable when in position in back of the tooth line to introduce fluid from the reservoir through the root canal and into the living body tissue.

2. Apparatus as described in claim 1 in which said fluid input means includes a valve means to permit fluid to pass in one direction into the living body tissue.

3. Apparatus as described in claim 2 in which there are a plurality of valve means, each locatable within a different tooth crown within a living body and each being in communication with a respective unobstructed root canal.

4. Apparatus as described in claim 1 comprising in addition:
   a partial denture plate having clips for mounting to teeth within the mouth of a body;
   said reservoir being flexible and being adapted to be filled with fluid which upon compression of the reservoir will pass through the root canal into the body tissue; and
   said reservoir being adapted to be located covering the palate in the mouth behind the upper tooth line.

5. Apparatus for injecting medicinal fluid into the blood system of a living body that has a plurality of teeth, each with a crown portion and an unobstructed root canal passing from the tooth crown to the end of the root comprising:
   fluid injection means constructed and adapted to be positioned entirely within the body mouth in back of the tooth line including;
   a valve injection means adapted to be secured within the crown portion of a tooth in communication with an unobstructed root canal passing through the tooth;
   said valve injection means comprising a one-way valve having a spring urged ball in a normal closed position and being operable to an open position to permit medication fluid to pass through to the tooth canal;
   a denture plate having clips for mounting the injection means to the upper teeth within the mouth of the body;
   a flexible reservoir adapted to be filled with medication fluid which upon compression of the reservoir will pass through the valve injector means and through the root canal to the body tissue.

6. A method of introducing general body medicinal drugs into a living body comprising the steps of;
   removing substantially all of the pulp tissue from the root canal of a tooth in the mouth of the body to provide a substantially unobstructed path from the crown and through the entire length of the root portion of the tooth to the mouth tissue;
   sealing the root canal at the tooth crown end with a seal adapted to be selectively opened when it is desired to inject a medicinal drug into the body; and
   selectively opening said seal and introducing medicinal drugs into the body through the unobstructed root canal to the mouth tissue whereby the said medicinal drug may diffuse into the body blood stream.

7. A method of introducing general medicinal drugs into a living body as set forth in claim 6 comprising the additional step of;
   periodically at various times selectively opening said seal and introducing medicinal drugs into the body through the root canal.

* * * * *